United States Patent [19]

Maes

[11] 4,387,166

[45] Jun. 7, 1983

[54] IMMUNOASSAY WHEREIN IMMUNE COMPLEX FORMS AND AGES FOR AT LEAST ONE HOUR

[75] Inventor: Roland F. Maes, Strasbourg, France

[73] Assignee: Anda Biologicals, Strasbourg, France

[21] Appl. No.: 302,589

[22] Filed: Sep. 15, 1981

[51] Int. Cl.³ ............................................. G01N 33/54
[52] U.S. Cl. ................................... 436/541; 436/517; 436/519; 436/520; 436/813; 436/814; 436/817; 436/818; 436/826
[58] Field of Search ........................ 23/230 B; 424/12; 436/517, 519, 520, 541, 826

[56] References Cited

U.S. PATENT DOCUMENTS 3,887,697  6/1975  Vyas .................................... 424/3 X
4,205,954  6/1980  Babson ............................... 436/517
4,308,026 12/1981  Mochida ............................ 424/12 X

OTHER PUBLICATIONS

"Methods in Enzymology", S. P. Colowick et al., eds., vol. 70, entitled Immunochemical Techniques, H. Van Vunakis et al., eds., pp. 462, 463, contributed by F. L. Adler et al., Academic Press, New York, 1980.
Chemical Abstracts, 81:87587r, (1974).

Primary Examiner—Sidney Marantz
Attorney, Agent, or Firm—William J. Daniel

[57] ABSTRACT

The sensitivity of hemagglutination inhibition tests is improved by introducing a determined amount of lyophilized antigen or antibody into serological tubes in the absence of the indicator component. The test fluid to be analyzed is incubated solely in the presence of its binding partner in a liquid phase. After completion of the binding reaction (about 5 hours but extendable to 18 hours), the sensitized indicator solid phase, usually consisting of sensitized red blood cells, is added. By this process a 10 to 20 fold increase in sensitivity of the hemagglutination inhibition test is routinely achieved.

7 Claims, No Drawings

IMMUNOASSAY WHEREIN IMMUNE COMPLEX FORMS AND AGES FOR AT LEAST ONE HOUR

FIELD OF THE INVENTION

This invention relates to an improvement in the sensitivity of immunological tests based on the interaction of an antigen and antibody with a sensitized solid phase such as sensitized blood cells, polymer particles and the like.

BACKGROUND OF THE INVENTION

The determination of substances for diagnostic or scientific purposes in liquid test samples by means of agglutination and the inhibition of agglutination of a sentized solid phase, such as red blood cells, colloidal particles, latex or the like is known for more than 20 years. The test proceeds as follows: the solid carrier phase is activated by a binding agent (e.g. tannic acid, glutaraldehyde, difluoro-dinitro benzene) and sensitized by an antigen or an antibody. It may also spontaneously adsorb the sensitizing substance.

The sensitized solid phase is mixed with the test liquid containing the soluble antigen or antibody to be determined and with a determined amount of a specific antibody or antigen with which the sensitized solid phase reacts in binding reaction. In the absence of foreign soluble antigen in the test liquid, an antigen-sensitized solid phase will be agglutinated by the specific antibody. In the presence of foreign soluble antigen, the latter will inhibit agglutination of the solid phase. Conversely, an antibody-sensitized solid phase will be agglutinated in the presence of a determined amount of specific antigen absent any foreign antigen and this agglutination will be inhibited when foreign soluble antibody is also present in the reacting medium from the test liquid.

This system, commonly referred to as the hemagglutination inhibition test (HAI), is relatively sensitive, but has lately been superseded by more refined techniques amount which radio-immuno-assay is outstanding. Radio-immuno-assays, however, require radioelements, expensive instrumentation and skilled labor, and it would be desirable to improve the HAI tests and increase their sensitivity, so that they can accomplish the same function as radio-immuno-assays at a much reduced cost.

GENERAL DESCRIPTION OF THE INVENTION

The present invention concerns a process for the detection of antigens such as human luteinizing hormone (LH), human chorionic gonadotropin (HCG), alpha-foeto-protein ($\alpha$FP), progesterone, testosterone, carcino-embryonic antigen (C.E.A.), acid phosphatase and others, by immunological means and also concerns the specific application of this process to the detection of ovulation and tumors.

Up until now, no hemagglutination tests have been described which apply to the ovulation hormone (luteinizing hormone, LH) or to tumor markers such as $\beta$-HCG, alpha-foeto-protein ($\beta$FP), carcino-embryonic antigen (C.E.A.) and others.

The main reason for this absence of a reliable test is the low concentration of these markers and hormones in plasma, urine, cephalo-rachidian fluid and other body fluids.

To illustrate this situation, and without this example being intended to be in any way limitative, take the case of the luteinizing hormone (LH), which is, in the female human being and in other mammals, an index or indicator of ovulation. Human LH is normally secreted at the 14th day of the menstrual cycle although women at other times of their cycle and also men continuously have low amounts of this hormone in circulation. This hormone is very similar to the pregnancy hormone (human chorionic gonadotropin) secreted from the moment of fertility and also by some tumors.

Both of these protein hormones possess the sub-unit $\alpha$. They differ slightly in that the sub-unit $\beta$, hydrogen-bound to the sub-unit $\alpha$, is shorter by 21 amino-acids in LH, as compared to NCG.

Pregnancy tests detecting the $\alpha$ and $\beta$ sub-units of NCG are well known. These immunological tests, as well as more specific tests relying on the use of antibodies against LH, have potential usefulness for the detection of LH. Also, specific pregnancy tests detecting the $\beta$ sub-unit of the hormone, have potential usefulness for detecting $\beta$ HCG-secreting tumors. However, up to the present, only expensive and complicated radio-immunoassays are employed for the detection of low levels of $\beta$ HCG or of LH.

The reason why a simple HAI test has not been used for this purpose is found in the very low levels of LH available at the peak of its secretion in ovulating females, and the low level of tumor markers secreted by tumors at their onset, precisely when it is of highest importance to detect them. Conventional HAI are simply not sensitive enough to detect these low levels of LH.

A conventional immunological HAI test for the detection of $\beta$ HCG or of LH is carried out in the following way: urine or other body test fluids containing the antigen to be determined is added to a mixture of antigen-sensitized indicator cells (in general, antigen-sensitized sheep cells) and specific antibodies at suitable dilution. If the test fluid is devoid of foreign antigen, the specific antibodies present in the mixture will agglutinate the red blood cells and these will sediment in a uniform mat. If the test fluid contains foreign antigen, this antigen will react with the specific antibody, an inhibition of agglutination will occur and the sensitized indicator cells will freely sediment in a small round button.

This procedure allows the detection of no more than about 125 international units of HCG/liter and 275 IU of LH/liter. Since small tumors secrete only minute amounts of HCG (detectable by a $\beta$ specific pregnancy test) equivalent to 15 to 50 IU HCG/liter and since at the peak of the LH secretion, i.e. on the 14th day after the beginning of the menstrual period, the minimal amount of LH present in plasma or urine is 40 IU LH/liter, available HAI tests for the detection of HCG and of LH lack sufficient sensitivity for the reliable detection of ovulation in a normally menstruating female or for the detection of tumor markers, when tumors begin to grow. For these purposes, only expensive radio-immuno-assays or enzymo-immuno-assays are suitable.

In a very surprising way, it has been found that the limit of sensitivity of hemagglutination inhibition tests can be lowered by a factor of 10 to 20 simply by delaying the moment at which the indicator component, i.e. the sensitized red blood cells or other solid phase are added to the antigen-antibody reaction mixture. It has been found that the proteases present in the body test fluids (plasma, serum, urine, cephalo-rachidian fluid, etc.) are not active enough to significantly interfere with the antigen-antibody reaction during the prolonged time needed for the reaction to come to completion. Furthermore and for the system to gain an increased reliability, it has been found that the reactant containing the antibodies may include a protease inhibitor and also bacteriostats or bactericides, such as sodium azide, merthiolate, trasylol, Di-isopropyl-fluoro-phosphate (DFP), ethylene-diamine tetra=acetic acid (EDTA) or other that will inhibit the activity of proteases and bacteria during the time of the immunological reaction, without however impairing that reaction.

Typically, a predetermined amount of specific antibodies against the antigen to be determined (e.g., $\beta$ HCG, $\alpha$ FP, C.E.A., acid phosphatase, etc.) diluted in a suitable reactant is provided in liquid form, and preferably lyophilized for greater stability during storage. To these specific antibodies are added the test fluid (e.g., 0.1 to 0.15 ml) containing the antigen to be determined. Instead of immediately adding to the mixture the sensitized indicator component (i.e. sensitized polymer beads or sensitized latex or sensitized red blood cells or the like) and reading the results of the complex reaction immediately as an aggregation or after settling of the solid phase into a distinctive agglutination pattern, the addition of the indicator system is postponed until a later time. Antigen and specific antibodies in liquid phase are thus left to react at a suitable temperature, usually room temperature. The length of time allowed for the primary reaction to take place before the addition of the sensitized indicator component defines the level of sensitivity of the test but should range from about 5 hours up to about 18 hours. The indicator component consists in an antigen-sensitized or an antibody-sensitized solid phase, dependent upon whether an antibody or an antigen is to be detected.

The following examples serve to illustrate the usefulness of the invention, without however being limitative:

EXAMPLE I

Male human urine was admixed with HCG at a series of test concentrations ranging from 200 IU/liter down to 7.5 IU/liter.

Antibodies against the $\beta$ subunit of HCG, obtained by innoculation of the $\beta$ subunit in rabbits, were diluted in a suitable solvent in order to obtain, in a HAI test with HCG-sensitized sheep cells, a sensitivity of 100 IU HCG/liter of analyzed fluid.

Fifty microliters of the antibodies solution, containing $10^{-3}$ M Diisopropyl fluorophosphate as a protein inhibitor, were dispensed in individual serology tubes and lyophilized before use. For a HCG determination, the test tubes each received a determined dose of HCG in 0.14 ml male urine. The tubes were left at R.T. for several hours and, at determined intervals, HCG-sensitized red blood cells suspended in 0.25 ml reaction were added to some tubes.

Table 1 illustrates the level of sensitivity attained in the course of time.

TABLE 1

| HCG in urine | DELAY IN ADDITION OF SENSITIZED INDICATOR CELLS IN HOURS | | | | | | | |
|---|---|---|---|---|---|---|---|---|
| IU/liter | 0 | 0.5 | 1 | 2 | 3 | 5 | 7 | 16 |
| 200 | 1 | — | — | — | — | — | — | — |
| 100 | 3 | 3 | 2 | 1 | 1 | 1 | 1 | — |
| 50 | 4 | 3 | 3 | 2 | 2 | 2 | 2 | — |

TABLE 1-continued

| HCG in urine | DELAY IN ADDITION OF SENSITIZED INDICATOR CELLS IN HOURS | | | | | | | |
|---|---|---|---|---|---|---|---|---|
| IU/liter | 0 | 0.5 | 1 | 2 | 3 | 5 | 7 | 16 |
| 25 | 4 | 4 | 3 | 3 | 3 | 3 | 3 | — |
| 20 | — | — | — | — | — | — | — | 2 |
| 12.5 | 4 | 4 | 4 | 4 | 3+ | 3 | 3 | — |
| 10 | — | — | — | — | — | — | — | 3 |
| 5 | — | — | — | — | — | — | — | 3 |
| 2.5 | — | — | — | — | — | — | — | 4 |
| 1.25 | — | — | — | — | — | — | — | 4 |
| 0 | 4 | 4 | 4 | 4 | 4 | 4 | 4 | 4 |

In this table, a positive inhibitory agglutinating reaction, i.e. presence of HCG in the analyzed fluid, is indicated by numerals ranging from 0 to 3, zero meaning a strong positive reaction and 3 a weak one. A negative reaction, i.e. absence of HCG, is noted by 4, meaning full agglutination.

It is observed that the HAI test, when carried out in the usual manner, i.e. with the immediate addition of the solid indicator phase together with the reacting fluid to the antibodies at time 0, sensitive to 100 IU HCG/liter of urine. This sensitivity is roughly the best one can expect for the conventional HAI test. The results of the test increase strikingly in sensitivity, however, when the addition of the indicator system is delayed at least 2–3 hours and preferably 5 hours or longer.

A 20 fold increase in sensitivity is thus attained when the primary antigen-antibody reaction in liquid phase is allowed to proceed overnight. This level of sensitivity is equal to the best radio-immuno-assays presently available on the market, and the improved HAI test of this invention is thus applicable for the detection of amounts of HCG comparable to that secreted by small tumors.

The cost of a determination of $\beta$ HCG by this improved HAI test, the length of time needed to perform it, the degree of skill required by the technician all compare extremely favorably to $\beta$ HCG-radio-immuno-assays or $\beta$ HCG-enzyme-immuno-assays.

EXAMPLE II

Antibodies were obtained in rabbits against the $\alpha$ subunit of HCG, which is known to be identical to the $\alpha$ subunit of LH. Fifty microliters of a suitable dilution of antibodies containing $10^{-3}$ M Diisopropyl fluoro phosphate (DFP) and 0.4% EDTA were lyophilized in individual serology tubes. After lyophilization, the tubes received 0.15 ml of male urine containing various amounts of LH or of HCG. Incubation proceeded for 18 hours at RT, after which 0.25 ml of a suspension of sensitized indicator red blood cells were added to all the tubes. Sedimentation of the cells was allowed at RT for 2 hours, after which the settled pattern of sedimentation was recorded. Results are summarized in Table 2 where 4 means full agglutination, i.e. no antigen present in the analyzed fluid and 3 to 0 means increasingly reduced agglutination and thus the presence of antigen in the analyzed fluid.

TABLE 2

| HCG concentration in IU/liter | Sensitivity | LH concentration in IU/liter | Sensitivity |
|---|---|---|---|
| 50 | 2 | 100 | 2 |
| 25 | 2 | 50 | 3 |
| 12.5 | 3 | 25 | 4— |
| 6.25 | 4 | 12.5 | 4 |
| 0 | 4 | 0 | 4 |

It is observed that the test is more sensitive to HCG than to LH. The concentration of LH in the analyzed fluid is detected without ambiguity down to 50 IU/liter and the test is sensitive to 25 IU/liter. This extremely high sensitivity makes the test applicable for the detection of ovulation.

EXAMPLE III

As disclosed in my application Ser. No. 284,686 filed July 20, 1981 for "Bacteria As Solid Carrier for Sensitizing Agents and Uses of Sensitized Bacteria", *E. Coli* bacteria were sensitized with HCG. Antibodies against HCG were obtained by innoculation of HCG into rabbits and bleeding 14 days after a booster innoculation of the antigen.

There was prepared a dilution of HCG antibodies contained in 50 microliters of diluent and supplemented with $10^{-3}$ M DFP and 0.4% EDTA which was sufficient to produce inhibition of the aggregation of the HCG-sensitized bacterial suspension, assayed in 50 microliters of diluent (0.1 M glycine, pH 8.0 containing 1% bovine serum albumin and 0.1% sodium azide), that would otherwise occur when the suspension is mixed together with 50 microliters of male urine containing 500 IU HCG/liter. At a lower concentration of HCG, the bacterial suspension underwent an aggregation.

Fifty microliter samples of the antibodies solution were placed in individual serology tubes, stoppered and kept at 4° C. until the time of use.

For the test, 50 microliter samples of urine containing various amounts of HCG ranging from 500 to 62.5 IU/liter were each added to the antibodies solution contained in one of the test tubes and left at room temperature (RT). At determined intervals, 50 microliters of a HCG-sensitized bacterial suspension were added to the antigen-antibody reaction tube, and the totality of the mixture (0.15 ml) was then immediately transferred on a glass slide, where it was slowly kept in motion by tilting for 3 minutes, after which time the aggregation or lack of aggregation of the bacterial suspension was observed and recorded. A positive test, i.e. indicating the presence of soluble HCG, was denoted by an inhibition of aggregation and a negative test, i.e. absence of detectable amounts of soluble HCG, was denoted by an aggregation of the sensitized bacterial suspension. Table 3 records the results of this experiment.

TABLE 3

| HCG in urine | INTERVAL BEFORE ADDITION OF SOLID INDICATOR PHASE (MIN) | | | | |
|---|---|---|---|---|---|
| IU/liter | 0 | 15 | 30 | 45 | 60 |
| 500 | pos. | pos. | pos. | pos. | pos. |
| 250 | neg. | pos. | pos. | pos. | pos. |
| 125 | neg. | neg. | neg. | dubious | pos. |
| 62.5 | neg. | neg. | neg. | neg. | neg. |
| 0 | neg. | neg. | neg. | neg. | neg. |

From this table, it is apparent that the delay in addition of the sensitized solid phase to the primary antibody-antigen reaction favors a higher sensitivity of the test.

A 15 minute delay doubles the sensitivity and a 60 min. delay increases the sensitivity fourfold.

For practical applications, several modes of operation are foreseen.

The specific antibodies and the indicator phase may be furnished in liquid form and in suspension respectively in two separate vials containing suitable inhibitors of proteases and bacteriostatic or bactericidal agents. The dilutions and dispensing required to obtain an optimum sensitivity with the test are left to be made by the technician, and this approach is thus restricted for use in clinics and laboratories.

Antibodies prediluted at an adequate level may be dispensed in individual serology tubes. They may further be lyophilized for increased shelf life. The provision of antibodies in exact determined proportions is preferred because the level of antibodies must be correctly adjusted for optimal results. All that one need then do is to add to the test tube a determined amount of the test fluid to be analyzed, wait for the primary reaction to be completed and after a specified interval add the indicator component.

If the test is intended for use by unskilled persons, a preferred test procedure is to provide the appropriate number of serology tubes containing the amount of lyophilized specific antibodies needed for optimal results. If the indicator component is to consist of sensitized red blood cells, the tubes are preferably inserted over a mirror. Plastic pouches or vials containing the exact amount of sensitized indicator solid phase suspended in the exact amount of liquid medium required to perform each test (usually 0.25 to 0.3 ml), are furnished in a number equal to that of the test tubes. The user has then to perform the following steps:

(1) add 2 or 3 drops of urine to a tube;
(2) wait 5 to 7 hours or longer, depending on the level of sensitivity desired;
(3) add the content of a pouch to the tube;
(4) Wait 2 hours and read the sedimented pattern over the mirror.

Obviously, the precision with which the results of the present tests are evaluated depends somewhat upon the skill and experience of the observer in evaluating the onset and extent of agglutination inhibition. Therefore, a skilled observer may well be able to detect a significant inhibition of agglutination with a shorter interval before the solid phase indicator is added whereas a person without training or experience would be advised to prolong the waiting period to insure maximum results, bearing in mind also that different antigens or antibodies may be subject to different levels of sensitivity. As a consequence, the minimum length of the waiting period is to be determined by several factors, namely the sensitivity of the particular binding reaction, the skill of the observer and the criticality of the need for the test information. In an emergency situation with a professional technician, useful results might be possible with only a one hour waiting period although 2-3 hours would ordinarily be preferable, especially as a confirmation. On the other hand, for purposes of a self-administered in-home pregnancy test, a waiting period of 18-24 hours would be optimum to eliminate uncertainty of the results as far as possible.

What is claimed is:

1. A process for detecting the presence in a body fluid to be tested of an antigen or an antibody by means of an immunological antigen-antibody binding reaction characterized by the steps of:
   (a) contacting the test fluid with a soluble specific antigen or specific antibody for the antibody or antigen to be detected under conditions conducive to a binding reaction therebetween and
   (b) after passage of a determined time interval of at least about one hour following step (a) adding to the mixture of step (a) a sensitized solid indicator phase capable of a binding reaction with the antibody or antigen respectively to be detected.

2. The process according to claim 1 wherein the sensitized indicator phase is in the form of solid beads or particles.

3. The process according to claim 1 where the solid indicator phase consists essentially of sensitized red blood cells or bacteria.

4. The process according to claim 1 characterized in that specific antibodies or antigens are lyophilized in predetermined amounts in individual containers.

5. The process according to claim 1 wherein said time interval is at least about 2–3 hours.

6. The process according to claim 5 wherein said time interval is in the range of about 5–18 hours.

7. The process according to claim 1 where the mixture of step (a) contains a protease inhibitor, a bacteriostat or a bactericide.

* * * * *